(12) United States Patent
Tang et al.

(10) Patent No.: US 6,706,693 B1
(45) Date of Patent: Mar. 16, 2004

(54) VACCINATION BY TOPICAL APPLICATION OF GENETIC VECTORS

(75) Inventors: De-chu Tang, Birmingham, AL (US); Donald H. Marks, Rockaway, NJ (US); David T. Curiel, Birmingham, AL (US); Zhongkai Shi, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 512 days.

(21) Appl. No.: 09/402,527

(22) PCT Filed: Aug. 13, 1998

(86) PCT No.: PCT/US98/16739
§ 371 (c)(1),
(2), (4) Date: Jan. 3, 2000

(87) PCT Pub. No.: WO99/08713
PCT Pub. Date: Feb. 25, 1999

Related U.S. Application Data

(60) Provisional application No. 60/055,520, filed on Aug. 13, 1997, and provisional application No. 60/075,113, filed on Feb. 11, 1998.

(51) Int. Cl.⁷ .................. A61K 48/00; C12N 15/63; C12N 15/79
(52) U.S. Cl. .................. 514/44; 435/320.1; 435/325; 435/455; 435/456; 424/59
(58) Field of Search .................. 514/44; 435/325, 435/320.1, 455, 456; 424/59

(56) References Cited

U.S. PATENT DOCUMENTS

| | | |
|---|---|---|
| 3,608,030 A | 9/1971 | Tint |
| 3,837,340 A | 9/1974 | Counter |
| 3,906,092 A | 9/1975 | Hilleman et al. |
| 3,950,512 A | 4/1976 | Emery et al. |
| 3,962,424 A | 6/1976 | Zygraich et al. |
| 4,089,801 A | 5/1978 | Schneider |
| 4,217,344 A | 8/1980 | Vanlerberghe et al. |
| 4,235,871 A | 11/1980 | Papahadjopoulos et al. |
| 4,241,046 A | 12/1980 | Papahadjopoulos et al. |
| 4,394,448 A | 7/1983 | Szoka, Jr. et al. |
| 4,405,616 A | 9/1983 | Rajadhyaksha |
| 4,557,934 A | 12/1985 | Cooper |
| 4,775,630 A | 10/1988 | Tibbetts et al. |
| 4,797,368 A | 1/1989 | Carter et al. |
| 4,806,350 A | 2/1989 | Gerber |
| 4,863,970 A | 9/1989 | Patel et al. |
| 4,929,442 A | 5/1990 | Powell |
| 5,023,252 A | 6/1991 | Hseih |
| 5,139,941 A | 8/1992 | Muzyczka et al. |
| 5,206,163 A | 4/1993 | Renard et al. |
| 5,494,807 A | 2/1996 | Paoletti et al. |
| 5,505,945 A | 4/1996 | Gristina et al. |
| 5,547,932 A | 8/1996 | Curiel et al. |
| 5,552,309 A | 9/1996 | March |
| 5,580,859 A | 12/1996 | Felgner et al. |
| 5,589,466 A | 12/1996 | Felgner et al. |
| 5,593,972 A | 1/1997 | Weiner et al. |
| 5,635,380 A | 6/1997 | Naftilan et al. |
| 5,658,785 A | 8/1997 | Johnson |
| 5,665,362 A | 9/1997 | Inglis et al. |
| 5,670,488 A | 9/1997 | Gregory et al. |
| 5,679,647 A | 10/1997 | Carson et al. |
| 5,693,622 A | 12/1997 | Wolff et al. |
| 5,698,443 A | 12/1997 | Henderson et al. |
| 5,700,470 A | 12/1997 | Saito et al. |
| 5,700,680 A | 12/1997 | Newton et al. |
| 5,700,910 A | 12/1997 | Metzger et al. |
| 5,703,055 A | 12/1997 | Felgner et al. |
| 5,705,151 A | 1/1998 | Dow et al. |
| 5,707,618 A | 1/1998 | Armentano et al. |
| 5,707,812 A | 1/1998 | Horn et al. |
| 5,716,613 A | 2/1998 | Guber et al. |
| 5,718,902 A | 2/1998 | Yilma et al. |
| 5,731,181 A | 3/1998 | Kmiec |
| 5,736,387 A | 4/1998 | Paul et al. |
| 5,739,118 A | 4/1998 | Carrano et al. |

(List continued on next page.)

FOREIGN PATENT DOCUMENTS

EP        0 773 295 A2      5/1997

OTHER PUBLICATIONS

Sarphie et al., "Bioavailability following transdermal powderd delivery (TPD) of radiolabeled inulin to hairless guinea pigs", Journal of Controlled Release, vol. 47, pp. 61–69, 1997.

Todryk et al., "Induction of immune responses to functional determinants of a cell surface streptococcal antigen", Immunology, vol. 87, pp. 55–63, 1996.

Yokoyama et al., "DNA immunization: Effects of vehicle and route of administration on the induction of protective antiviral immunity", FEMS Immunology and Medical Microbiology, vol. 14, pp. 221–230, 1996.

(List continued on next page.)

*Primary Examiner*—Deborah Crouch
(74) *Attorney, Agent, or Firm*—Frommer Lawrence & Haug LLP; William S. Frommer; Thomas J. Kowalski

(57) ABSTRACT

The present invention provides a method of inducing an immune response in a non-invasive mode, comprising the step of: contacting skin of an individual in need of such treatment topically by applying to said skin an immunologically effective concentration of a genetic vector encoding a gene of interest. Also provided is a method of inducing an anti-tumor immune response in an animal in need of such treatment, comprising the step of: contacting skin of said animal topically by applying to said skin an immunologically effective concentration of a vector encoding a gene which encodes an antigen which induces an anti-tumor effect in said animal following administration. The genetic vector may include adenovirus recombinants, DNA/adenovirus complexes, DNA/liposome complexes, or any other vectors capable of expressing transgenes. Topical application of geneticvectors may preferably include a device as designed therein.

3 Claims, 12 Drawing Sheets

U.S. PATENT DOCUMENTS

| | | |
|---|---|---|
| 5,753,263 A | 5/1998 | Lishko et al. |
| 5,753,500 A | 5/1998 | Shenk et al. |
| 5,756,086 A | 5/1998 | McClelland et al. |
| 5,762,939 A | 6/1998 | Smith et al. |
| 5,763,270 A | 6/1998 | Eastman et al. |
| 5,766,599 A | 6/1998 | Paoletti et al. |
| 5,770,442 A | 6/1998 | Wickham et al. |
| 5,780,280 A | 7/1998 | Lebkowski et al. |
| 5,786,211 A | 7/1998 | Johnson |
| 5,789,390 A | 8/1998 | Descamps et al. |
| 5,792,462 A | 8/1998 | Johnston et al. |
| 5,795,972 A | 8/1998 | Kmiec |
| 5,804,566 A | 9/1998 | Carson et al. |
| 5,817,492 A | 10/1998 | Saito et al. |
| 5,817,637 A | 10/1998 | Weiner et al. |
| 5,820,868 A | 10/1998 | Mittal et al. |
| 5,824,538 A | 10/1998 | Branstrom et al. |
| 5,824,544 A | 10/1998 | Armentano et al. |
| 5,830,177 A | 11/1998 | Li et al. |
| 5,830,463 A | 11/1998 | Duke et al. |
| 5,830,730 A | 11/1998 | German et al. |
| 5,846,559 A | 12/1998 | Hopp |
| 5,849,719 A | 12/1998 | Carson et al. |
| 5,851,806 A | 12/1998 | Kovesdi et al. |
| 5,872,005 A | 2/1999 | Wang et al. |
| 5,872,154 A | 2/1999 | Wilson et al. |
| 5,874,279 A | 2/1999 | Cochran et al. |
| 5,882,877 A | 3/1999 | Gregory et al. |
| 5,885,808 A | 3/1999 | Spooner et al. |
| 6,087,341 A | 7/2000 | Khavari |

OTHER PUBLICATIONS

Niemic et al., "Perifollicular Transgenic Expression of Human Interleukin–1 Receptor Antagonis Protein following Topical Application of Novel Liposome–Plasmid DNA Formulations In Vivo", Journal of Pharmaceutical Sciences, vol. 86, No. 6, Jun. 1997 pp. 701–708.

Weiner N., "Targeted follicular delivery of macromolecules via liposomes", International Journal of Pharmaceuticals, vol. 162, pp. 29–38, 1998.

Goldman et al., "In vitro and in vivo gene delivery mediated by a synthetic polycationic amino polymer", Nature Biotechnology, May 1997, vol. 15, pp. 462–466.

Lu et al., "Topical Application of Viral Vectors for Epidermal Gene Transfer", The Society for Investigative Dermatology, Inc., pp. 803–808, 1997.

Donnelley et al, "DNA Vaccines", Life Sciences, vol. 60, No. 3, pp. 163–172, 1997.

Paul et al., "Transdermal immunization with large proteins by means of ultradeformable drug carriers", Eur. J. Immunol., vol. 25, pp. 3521–3524, 1995.

Sawamura et al. "In Vivo Transfer of a Foreign Gene to Keratinocytes Using the Hemagglutinating Virus of Japan–Liposome Method", The Society for Investigative Dermatology, Inc., pp. 195–199, 1997.

Zhdanov et al., "Nonviral methods of gene transfer in gene therapy", Vopr Med Khim, vol. 43, No. 1, 1997 Jan. Feb., pp. 3–12 (Abstract).

Lee et al., "Control of immune responses by gene immunization", Ann. Med. vol. 5, pp. 46–0468, Oct. 1998 (Abstract).

Lee et al., "Induction of an antigen–specific, CD1–restricted cytotoxic T lymphocyte response In vivo", J. Exp. Med., vol. 187, No. 3, pp. 443–438, Feb. 2, 1998 (Abstract).

Corr et al., "Costimulation provided by DNA immunization enhances antitimor immunity", J. Immunol., vol. 159, No. 10, pp. 4999–5004, Nov. 15, 1997 (Abstract).

Lee et al., "Inhibititon of IgE antibody formation by plasmid DNA immunization is mediated by both CD4+ and CD8+ T Cells", Int. Arch Allergy Immunol., vol. 113, Nos. 103, pp. 227–230, May–Jul. 1997 (Abstract).

Corr et al., "Gene vaccination with naked plasmid DNA: mechanism of CTL priming", J. Exp. Med. vol. 184, No. 4, pp. 1555–1560, Oct. 1, 1996 (Abstract).

Sato et al., "Immunostimulatory DNA sequences necessary for effective intradermal gene immunization", Science, vol. 273, No. 5273, pp. 352–354, Jul. 19, 1996 (Abstract).

Raz et al., "Preferential induction of th1 immune response and inhibitIon of specific IgE antibody formation by plasmid DNA immunization", Proc. Nat'l. Acad. Sci. USA, vol. 93, No. 10, pp. 5141–5145, May 14, 1996 (Abstract).

Raz et al, "Intradermal gene immunization: the possible role of DNA uptake in the induction of cellular immunity to viruses", Proc. Natl. Acad. Sci. USA, vol. 91, No. 20., pp. 519–523, Sep. 27, 1994 (Abstract).

Krawczynski et al., "Effect of immune globulin on the prevention of experimental hepatitis C virus infection", J. Infect. Dis., vol. 173, No. 4, pp. 822–828, Apr. 1996 (Abstract).

Watanabe et al., "Induction of antibodies to a kappa V region by gene immunization", J. Immunol., vol. 151, No. 5, pp. 2871–2876, Sep. 1, 1993 (Abstract).

Silverman et al., "Structural characterization of the second major cross–reactive idiotype group of human rheumatoid factors. Association with the VH4 gene family", Arthritis Rheum., vol. 33, No. 9, pp. 1347–1360, Sep. 1990 (Abstract).

Carson, "Infectious diseases in day–care centers: transmission and approaches to prevention", Drug Intell. Clin. Pharm., vol. 21, No. 9, pp. 694–701, Sep. 1987, (Abstract).

Rhodes et al., "Autoantibodies in infectious mononucleosis have specificity for the glycine–alanine repeating region of the Epstein–Barr virus nuclear antigen", J. Exp. Med., vol. 165, No. 4, pp. 1026–1040, Apr. 1, 1987 (Abstract).

Fong et al., "The common occurrence of internal image type anti–idiotypic antibodies in rabbits immunized with monoclonal and polyclonal human IgM rheumatoid factors", Clin. Exp. Immunol., vol. 64, No. 3, pp. 570–580, Jun. 1986 (Abstract).

Goni et al., "Sequence similarities and cross–idiotypic specificity of L chains among human monoclonal IgM kappa with anti–gamma–globulin activity", J. Immunol., vol. 135, No. 6, pp. 4073–4079, Dec. 1985 (Aastract).

Chen et al., "Characterization of human–rheumatoid factors with seven antiidiotypes induced by synthetic hypervariable region peptides", J. Exp. Med., vol. 162, No. 2, pp. 487–500, Aug. 1, 1985, (Abstract).

Chen et al., "Characterization of an epibody. An antiidiotype that reacts with both the idiotype of rheumatoid factors (RF) and the antigen recognized by RF.", J. Exp. Med., vol. 161, No. 2, pp. 323–331, Feb. 1, 1985 (Abstract).

Chen et al., "Delineation of a cross–reactive idiotype on human autoantibodies with antibody against a synthetic peptide", J. Exp. Med., vol. 159, No. 5, pp. 1502–1511, May 1, 1984. (Abstract).

Chen et al., "Anti–hypervariable region antibody induced by a defined peptide: an approach for studying the structural correlates of idiotypes", Proc. Natl. Acad. Sci. USA, vol. 81, No. 6, pp. 1784–1788, Mar. 1984 (Abstract).

Welch et al., "Increased frequency of rheumatoid factor precursor B lymphocytes after immunization of normal adults with tetanuz toxoid", Clin. Exp. Immunol., vol. 51, No. 2, pp. 299–304, Feb. 1983 (Abstract).

Krul, "Advances in Gene Therapy: Clear Progress Despite Setbacks", Therapy Markets and Emerging Technologies Spectrum Publications, Issue 112, 47 pages, Dec. 20, 1996 (Abstract).

Press Release, "Perkin–Elmer and Kimeragen to Develop Novel Gene Repair Molecules That Treat Genetic Diseases", Norwalk, CT and Newtown, PA, Sep. 24, 1996.

Stephenson, "New Method to Repair Faulty Genes Stirs Interest in Chimeraplasty Technique", JAMA, vol. 282, No. 2, pp. 119–121, Jan. 13, 1999.

Li et al., Nature Medicine, vol. 1, No. 7, pp. 705–706, Jul. 7, 1995.

Lu et al., Proc. Assoc. Amer. Phys., vol. 108, No. 2, pp. 165–172, Mar. 1996.

English Abstract for European Patent Appln. No. 87–110213753, Pub. No. 00213753/EPA1, Pub. Date Mar. 11, 1987.

English Abstract for European Patent Appln. No. 84–340116472, Pub. No. 00116472/EPA2, Pub. Date Aug. 22, 1984.

Abstract for U.S. Patent No. 05662098 (Sep. 2, 1997).
Abstract for U.S. Patent No. 05648096 (Jul. 15, 1997).
Abstract for U.S. Patent No. 05645834 (Jul. 8, 1997).
Abstract for U.S. Patent No. 05616329 (Apr. 1, 1997).
Abstract for U.S. Patent No. 05530102 (Jun. 25, 1996).
Abstract for U.S. Patent No. 05505945 (Apr. 9, 1996).

J. Neurosci. Res., vol. 43, No. 1, pp. 32–41, Jan. 1, 1996 (Abstract).

Nat. Med., vol. 1, No. 5, pp. 481–481, May 1995 (Abstract).

J. Invest. Dermatol., vol. 108, No. 5, pp. 803–808, May 1997 (Abstract).

Citations from Biological Abstracts:BIO, Oct. 15, 1997.

English Abstract for German Patent No. DE 3937412.

English Abstract for International Patent No. WO 94/10323.

English Abstract for Canadian Patent No. 2,234,201.

English Abstract for European Patent Appln. No. 97–200773295, Pub. No. 00773295/EPA2, Pub. Date May 14, 1997.

English Abstract for European Patent Appln. No. 96–200711571, Pub. No. 00711571/EPA1, Pub. Date May 15, 1996.

English Abstract for European Patent Appln. No. 91–020406778, Pub. No. 00406778/EPA1, Pub. Date Jan. 9, 1991.

English Abstract for European Patent Appln. No. 89–090304786, Pub. No. 00304786/EPA2, Pub. Date Mar. 1, 1989.

English Abstract for European Patent Appln. No. 89–020298142, Pub. No. 00298142, Pub. Date Jan. 11, 1989.

English Abstract for European Patent Appln. No. 88–420286798, Pub. No. 00286798/EPA2, Pub. Date Oct. 19, 1988.

English Abstract for European Patent Appln. No. 88–080256190, Pub. No. 00213753/EPA1, Pub. Date Mar. 11, 1987.

DNA/Ad

DNA/Liposome

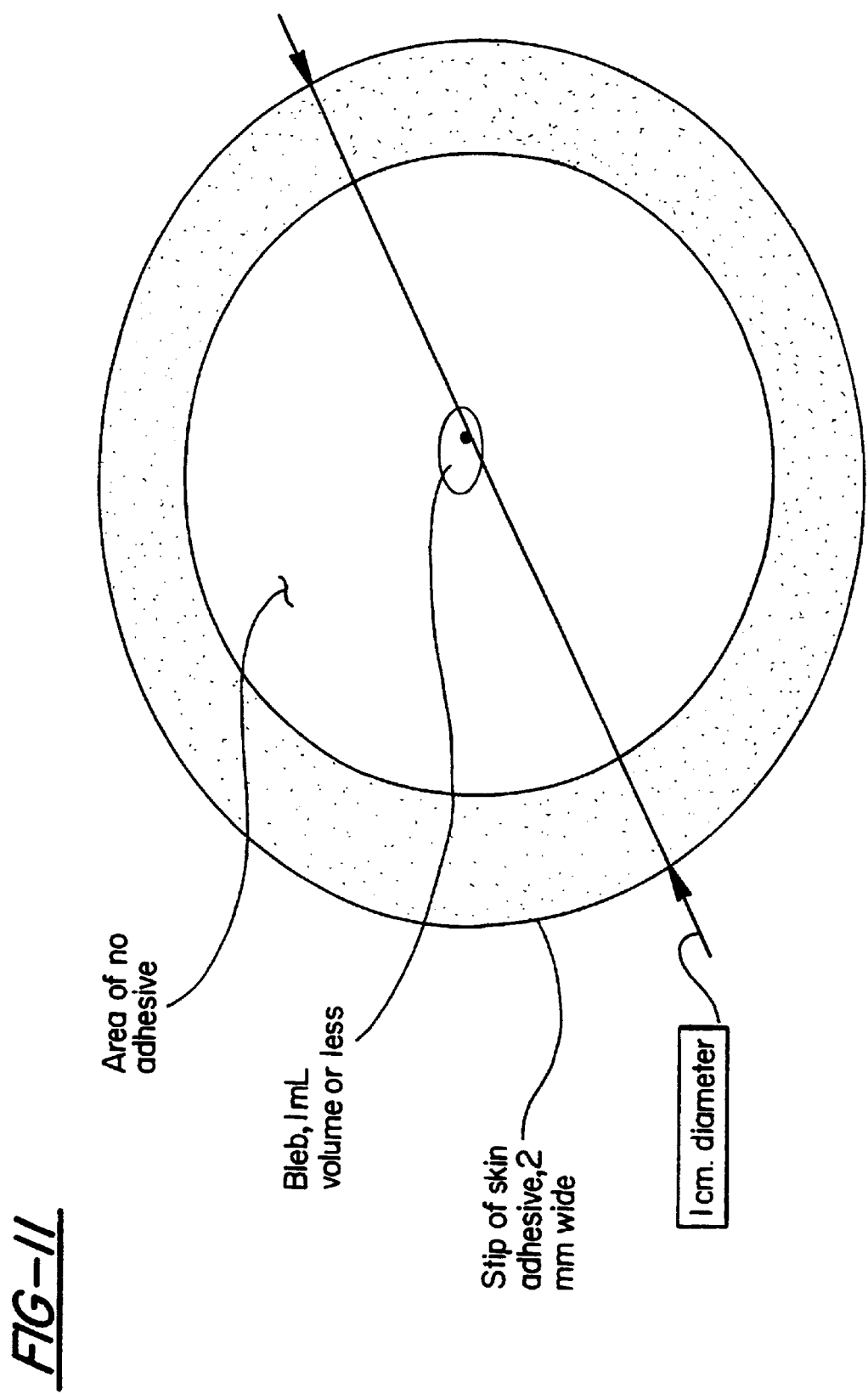

VACCINATION BY TOPICAL APPLICATION OF GENETIC VECTORS

This application claims priority of U.S. Provisional Application No. 60/055,520, filed Aug. 13, 1997 and U.S. Provisional Application No. 60/075,113, filed Feb. 11, 1998.

BACKGROUND OF THE INVENTION

1. Field of the Invention

The present invention relates generally to the fields of immunology and vaccine technology. More specifically, the present invention relates to techniques of skin-targeted non-invasive gene delivery to elicit immune responses and uses thereof.

2. Description of the Related Art

Activation of the immune system of vertebrates is an important mechanism for protecting animals against pathogens and malignant tumors. The immune system consists of many interacting components including the humoral and cellular branches. Humoral immunity involves antibodies that directly bind to antigens. Antibody molecules as the effectors of humoral immunity are secreted by B lymphocytes. Cellular immunity involves specialized cytotoxic T lymphocytes (CTLs) which recognize and kill other cells which produce non-self antigens. CTLs respond to degraded peptide fragments that appear on the surface of the target cell bound to MHC (major histocompatibility complex) class I molecules. It is understood that proteins produced within the cell are continually degraded to peptides as part of cellular metabolism. These fragments are bound to the MHC molecules and are transported to the cell surface. Thus the cellular immune system is constantly monitoring the spectra of proteins produced in all cells in the body and is poised to eliminate any cells producing non-self antigens.

Vaccination is the process of priming an animal for responding to an antigen. The antigen can be administered as a protein (classical) or as a gene which then expresses the antigen (genetic imimunization). The process involves T and B lymphocytes, other types of lymphoid cells, as well as specialized antigen presenting cells (APCs) which can process the antigen and display it in a form which can activate the immune system. Current modes for the administration of genetic vaccines has focused on invasive procedures including needle injections, scarification, and gene gun-mediated penetration. Inoculation of vaccines in an invasive mode requires equipment and personnel with special medical training, and is usually associated with discomfort and potential hazards (bleeding, infection). There is now evidence that the inoculation of vaccines in an invasive mode may be unnecessary (Tang et al., 1997; Glenn et al., 1998). Since the skin interfaces directly with the external environment and is in constant contact with potential pathogens, the immune system must constantly keep a mobilized biological army along the skin border for warding off potential infections. As a consequence, the outer layer of skin is essentially an immunocompetent tissue. Immunologic components present in the skin for the elicitation of both humoral and cytotoxic cellular immune responses include epidermal Langerhans cells (which are MHC class II-positive antigen-presenting cells), keratinocytes, and both $CD4^+$ and $CD8^+$ T lymphocytes. These components make the skin an ideal site for administration of vaccine. The large accessible area of skin and its durability are other advantages for applying vaccines to this tissue. Expression of a small number of antigens in the outer layer of skin without physical penetration may thus elicit a potent immune response by alarming the immune surveillance mechanism.

The efficacy of a vaccine is measured by the extent of protection against a later challenge by a tumor or a pathogen. Effective vaccines are immunogens that can induce high titer and long-lasting immunity for targeted intervention against diseases after a minimum number of inoculations. For example, genetic immunization is an approach to elicit immune responses against specific proteins by expressing genes encoding the proteins in an animal's own cells. The substantial antigen amplification and immune stimulation resulting from prolonged antigen presentation in vivo can induce a solid immunity against the antigen. Genetic immunization simplifies the vaccination protocol to produce immune responses against particular proteins because the often difficult steps of protein purification and combination with adjuvant, both routinely required for vaccine development, are eliminated. Since genetic immunization does not require the isolation of proteins, it is especially valuable for proteins that may lose conformational epitopes when purified biochemically. Genetic vaccines may also be delivered in combination without eliciting interference or affecting efficacy (Tang et al., 1992; Barry et al., 1995), which may simplify the vaccination scheme against multiple antigens. It has been demonstrated, as presented in this application, that genetic vaccines can be inoculated in a novel way as skin-targeted non-invasive vaccines. The combination of genetic vaccines with a non-invasive delivery mode may result in a new class of "democratic" vaccines that require no special skill and equipment for administration.

While topically-applied protein-based vaccines have been studied, their usefulness may be limited. Although topical application of protein-based vaccines in conjunction with cholera toxin may also immunize animals in the same non-invasive mode (Glenn et al., 1998) as skin-targeted non-invasive genetic vaccines have already been shown to do (Tang et al., 1997), the two classes of vaccines activate the immune system via different mechanisms. Further, the efficacy of genetic vaccines is in general superior to that of protein vaccines due to the de novo synthesis of antigens similar to natural infections (McDonnell and Askari, 1996). Although U.S. Pat. No. 3,837,340 describes a method for vaccinating animals by contacting skin with dried viruses, the viruses that they employ are not genetic vectors capable of expressing transgenes. In addition, the immunogen may be protein in the viral coat, instead of protein produced from expression of viral genes in animals' own cells.

The prior art of vaccination usually requires equipment, e.g., syringe needles or a gene gun, and special skill for the administration of vaccines. There is a great need and desire in the art for the inoculation of vaccines by personnel without medical training and equipment. A large number of diseases could potentially be immunized against through the development of non-invasive vaccination onto the skin (NIVS) because the procedure is simple, effective, economical, painless, and potentially safe. As a consequence, NIVS may boost vaccine coverages in developing countries where medical resources are in short supply, as well as in developed countries due to patient comfort. Infectious diseases caused by viruses, including AIDS and flu, by bacteria, including tetanus and TB, and by parasites, including malaria, and malignant tumors including a wide variety of cancer types may all be prevented or treated with skin-targeted non-invasive vaccines without requiring special equipment and medical personnel. The present invention satisfies this longstanding need and desire in the art.

SUMMARY OF THE INVENTION

Non-invasive vaccination onto the skin (NIVS) can improve vaccination schemes because skin is an immunocompetent tissue and this non-invasive procedure requires no specially trained personnel. Skin-targeted non-invasive gene delivery can achieve localized transgene expression in the skin and the elicitation of immune responses (Tang et al., 1997). These results indicate that NIVS is a novel and efficient method for the delivery of vaccines. The simple, effective, economical and painless immunization protocol of the present invention should make vaccination less dependent upon medical resources and, therefore, increase the annual utilization rate of vaccinations.

The present invention provides a method for immunizing animals comprising the step of skin-targeted non-invasive delivery of a preparation comprising genetic vectors, whereby the vector is taken up by epidermal cells and has an immunogenic effect on vertebrates. Also provided is a method for immunizing animals by a delivery device, comprising the steps of including genetic vectors in the delivery device and contacting the naked skin of a vertebrate with a uniform dose of genetic material confined within the device, whereby the vector is taken up by epidermal cells for expressing a specific antigen in the immunocompetent skin tissue. The genetic vector may be adenovirus recombinants, DNA/adenovirus complexes, DNA/liposome complexes or any other genetic vectors capable of expressing antigens in the skin of a vertebrate.

In one embodiment of the present invention, there is provided a method of inducing an immune response, comprising the step of: contacting skin of an individual or animal in need of such treatment by topically applying to said skin an immunologically effective concentration of a genetic vector encoding a gene of interest.

In another embodiment of the present invention, there is provided a method of inducing a protective immune response in an individual or animal in need of such treatment, comprising the step of: contacting the skin of said animal by topically applying to said skin an immunologically effective concentration of a vector encoding a gene which encodes an antigen which induces a protective immune effect in said individual or animal following administration.

In another embodiment, the invention presents a method for co-expressing transgenes in the same cell by contacting naked skin with DNA/adenovirus complexes. This protocol may allow the manipulation of the immune system by co-producing cytokines, costimulatory molecules, or other immune modulators with antigens within the same cellular environment.

The present invention also encompasses the use of a delivery device (bandages, adhesive dressings, or the like) for the delivery of skin-targeted non-invasive vaccines.

The present invention includes all genetic vectors for all of the uses contemplated in the methods described herein. Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 11 shows a device for the administration of skin-targeted non-invasive vaccines.

DETAILED DESCRIPTION OF THE INVENTION

Figure 1:
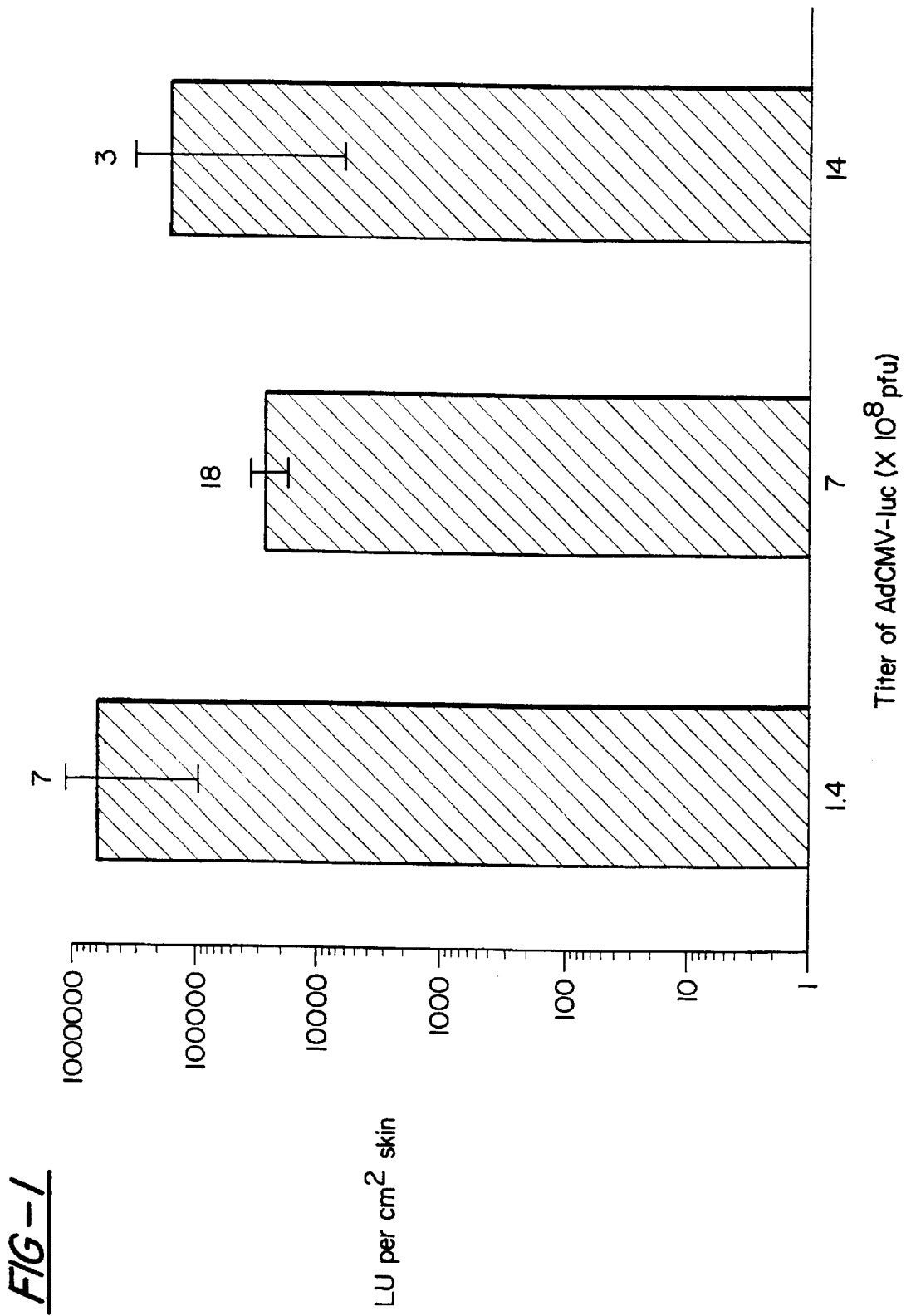
FIG. 1 shows the transgene expression from adenovirus recombinants in the skin by topical application of the vectors.

The present invention is directed to a method of inducing an immune response, comprising the step of contacting the outer layer of skin of an individual or animal in need of such treatment with an immunologically effective concentration of a genetic vector containing a gene of interest without physical invasiveness for a period of time suitable to elicit an immune response thereto. Representative examples of antigens which can be used to produce an immune response using the methods of the present invention include the human carcinoembryonic antigen, the HIV gp120, the tetanus toxin C-fragment, and the influenza HA and NP, etc. Most preferably, the immune response produces a protective effect against neoplasms or infectious pathogens.

The practice of the present invention requires delivering genetic vectors operatively coding for a polypeptide into the outer layer of skin of a vertebrate by a non-invasive procedure for immunizing the animal. These genetic vectors can be administered to the vertebrate by direct transfer of the genetic material to the skin without utilizing any devices, or by contacting naked skin utilizing a bandage or a bandage-like device. In preferred applications, the genetic vector is in aqueous solution. Vectors reconstituted from lyophilized powder are also acceptable. The vector may encode a complete gene, a fragment of a gene or several genes, gene fragments fused with immune modulatory sequences such as ubiquitin or CpG-rich synthetic DNA, together with transcription/translation signals necessary for expression.

In another embodiment of the present invention, the vector further contains a gene selected from the group consisting of co-stimulatory genes and cytokine genes. In this method the gene is selected from the group consisting of a GM-CSF gene, a B7-1 gene, a B7-2 gene, an interleukin-2 gene, an interleukin-12 gene and interferon genes.

In the embodiments of the invention that require use of adenovirus recombinants, it may include E1-defective, E3-defective, and/or E4-defective adenovirus vectors, or the "gutless" adenovirus vector in which all viral genes are deleted. The E1 mutation raises the safety margin of the vector because E1-defective adenovirus mutants are replication incompetent in non-permissive cells. The E3 mutation enhances the immunogenicity of the antigen by disrupting the mechanism whereby adenovirus down-regulates MHC class I molecules. The E4 mutation reduces the imnmunogenicity of the adenovirus vector by suppressing the late gene expression, thus may allow repeated re-vaccination utilizing the same vector. The "gutless" adenovirus vector is the latest model in the adenovirus vector family. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated for multiple times for re-vaccination. The "gutless" adenovirus vector also contains 36 kb space for acconmmodating transgenes, thus allowing co-delivery of a large number of antigen genes into cells. Specific sequence motifs such as the RGD motif may be inserted into the H-I loop of an adenovirus vector to enhance its infectivity. An adenovirus recombinant is constructed by cloning specific transgenes or fragments of transgenes into any of the adenovirus vectors such as those described above. The adenovirus recombinant is used to transduce epidermal cells of a vertebrate in a non-invasive mode for use as an immunizing agent.

In the embodiments of the invention that require use of DNA/adenovirus complexes, it requires plasmid DNA complexed with adenovirus vectors utilizing either PEI (polyethylenimine) or polylysine. The adenovirus vector within the complex may be either "live" or "killed" by UV irradiation. The UV-inactivated adenovirus vector as a receptor-binding ligand and an endosomolysis agent for facilitating DNA-mediated transfection (Cotten et al., 1992) may raise the safety margin of the vaccine carrier. The DNA/adenovirus complex is used to transfect epidermal cells of a vertebrate in a non-invasive mode for use as an immunizing agent.

In the embodiments of the invention that require use of DNA/liposome complexes, it requires materials for forming liposomes, and requires that DNA/liposome complexes be made from these materials. The DNA/liposome complex is used to transfect epidermal cells of a vertebrate in a non-invasive mode for use as an immunizing agent.

Genetic vectors provided by the invention can also code for immune modulatory molecules which can act as an adjuvant to provoke a humoral and/or cellular immune response. Such molecules include cytokines, co-stimulatory molecules, or any molecules that may change the course of an immune response. One can conceive of ways in which this technology can be modified to enhance still further the immunogenicity of antigens.

The genetic vector used for NIVS can take any number of forms, and the present invention is not limited to any particular genetic material coding for any particular polypeptide. All forms of genetic vectors including viral vectors, bacterial vectors, protozoan vectors, and DNA vectors, when used as skin-targeted non-invasive vaccine carriers, are within the methods contemplated by the invention.

The genes can be delivered by various methods including device-free topical application or coating the genes on the surface of the skin of an animal by a device such as a pad or bandage; e.g., an adhesive bandage. Referring to FIG. 11, a device for non-invasive vaccination is shown. This vaccine delivery device includes a non-allergenic, skin adhesive patch having a bleb disposed therein. In one embodiment, the patch is further comprised of plastic, approximately 1 cm in diameter. The vaccine can be disposed within the bleb. In another embodiment, the bleb contains approximately 1 mL of vaccine (as liquid, lyophilized powder with reconstituting fluid, and variants thereof). In a preferred embodiment, the surface of the bleb in contact with the skin is intentionally weaker than the opposite surface, such that when pressure is applied to the opposite surface, the lower surface breaks and releases the vaccine contents of the bleb onto the skin. The plastic patch traps the vaccine against the skin surface.

Dosage forms for the topical administration of the genetic vector and gene of interest of this invention can include liquids, ointments, powders, and sprays. The active component can be admixed under sterile conditions with a physiologically acceptable carrier and any preservatives, buffers, propellants, or absorption enhancers as may be required.

In terms of the terminology used herein, an immunologically effective amount is an amount or concentration of the genetic vector encoding the gene of interest, that, when administered to an animal, produces an immune response to the gene product of interest.

Various antigens may be delivered topically at different concentrations. Generally, useful amounts for adenovirus vectors are at least approximately 100 pfu and for plasmid DNA at least approximately 1 ng of DNA.

The methods of the invention can be appropriately applied to prevent diseases as prophylactic vaccination or treat diseases as therapeutic vaccination.

The vaccines of the present invention can be administered to an animal either alone or as part of an immunological composition.

Beyond the human vaccines described, the method of the invention can be used to immunize animal stocks. The term animal means all animals including humans. Examples of animals include humans, cows, dogs, cats, goats, sheep, and pigs, etc. Since the immune systems of all vertebrates operate similarly, the applications described can be implemented in all vertebrate systems.

The following examples are given for the purpose of illustrating various embodiments of the invention and are not meant to limit the present invention in any fashion.

Protocols

Mice and Cell Cultures

Inbred mice were maintained at the University of Alabama at Birmingham. Cells were cultured in RPMI 1640 or DMEM media containing 2% fetal bovine serum and 6% calf serum.

Topical Application of Genetic Vectors

Mice were anesthetized and hair and cornified epithelium covering a restricted area of abdominal or neck skin were removed by a depilatory (e.g., NAIR). Genetic vectors were pipetted onto the preshaved and NAIR-treated skin and kept in contact with naked skin for varying amounts of time (e.g., 1 hour to 18 hours). Vectors may be pipetted directly onto naked skin, or into a cylinder that is glued onto the skin.

Preparation of Adenovirus Vectors

High titer adenovirus stocks were prepared from human 293 cells infected with specific adenovirus recombinants. Lysates were subjected to ultracentrifugation through a cesium chloride gradient. Viral bands were extracted and dialyzed against 10 mM Tris (pH 7.5)/135 mM NaCl/5 mM KCl/1 mM $MgCl_2$. Purified viruses were filter sterilized with glycerol added to 10%, and stored in aliquots at −80° C. Titer for adenovirus stocks was determined by plaque assay.

Luciferase Assay

The amount of luciferase in the skin was determined as previously described (Tang, 1994). Briefly, a piece of excised skin was homogenized with a Kontes glass tissue grinder in lysis buffer. After removing tissue debris by centrifugation, luciferase activity in the skin extract was determined with a luminometer by measurement of integrated light emission in the presence of excess ATP and luciferin.

β-Galactosidase Assay

A piece of excised skin was quickly frozen in Tissue-Tek O.C.T. compound (Miles Laboratories Inc.) in liquid nitrogen and stored at −80° C. until use. The frozen tissue was cross sectioned at 4 μm, fixed in 4% paraformaldehyde, and stained for β-galactosidase activity by incubation in X-gal staining solution as previously described (Tang et al., 1994). Sections were counterstained with haematoxylin and eosin.

Preparation of DNA/Adenovirus Complexes

DNA/adenovirus complexes were prepared by mixing 100 μg plasmid DNA with $1 \times 10^{11}$ particles of adenovirus in the presence of the condensing agent polylysine for each application. The titer of adenovirus was determined by absorbance.

Preparation of DNA/Liposome Complexes

DNA/liposome complexes were prepared by mixing 100 μg plasmid DNA with 100 μg DOTAP/DOPE (1:1; Avanti) for each application. Plasmids were prepared using Qiagen Plasmid Maxi Kits.

Western Blot Analysis

Sera from tail bleeds were diluted 1:250 to 1:500 and reacted with purified proteins that had been separated in a SDS-polyacrylamide gel and transferred to an Immobilon-P membrane (Millipore). Reaction was visualized using the ECL kit (Amersham).

EXAMPLE 1

The present invention demonstrates that antigen genes can be delivered into the skin of mice in a simplified manner by skin-targeted non-invasive delivery of a genetic vector without using sophisticated equipment. FIG. 1 shows that substantial amounts of luciferase enzyme was produced after delivery of limited amounts of AdCMV-luc (an adenovirus vector encoding the firefly luciferase) (Tang et al., 1994) onto the skin. Ad, adenovirus; pfu, plaque-forming units; LU, light units. Results are the mean log[LU per $cm^2$ skin]±SE (n is shown on top of each column). Mice mock-applied or coated with an adenovirus vector that did not encode luciferase produced no detectable luciferase activity in the skin. The level of transgene expression from the adenovirus vector in the skin did not appear to correlate with the titer of the virus. It is possible that only a small number of cells can be transduced by the virus in a restricted subset of skin, and $10^8$ plaque-forming units (pfu) of adenovirus recombinants may have saturated the target cells. This variability could also be due, in part, to variations of individual mice. In addition, some of the variability probably arose from the procedure for removing cornified epithelium which had not been standardized (Johnston and Tang, 1994). The amount of antigen produced may potentially be amplified by applying more vectors onto a larger area.

EXAMPLE 2

Figure 2A:
FIGS. 2a and 2b show the characterization of potential target cells that can be transduced by topically-applied adenovirus recombinants.
Figure 2B:
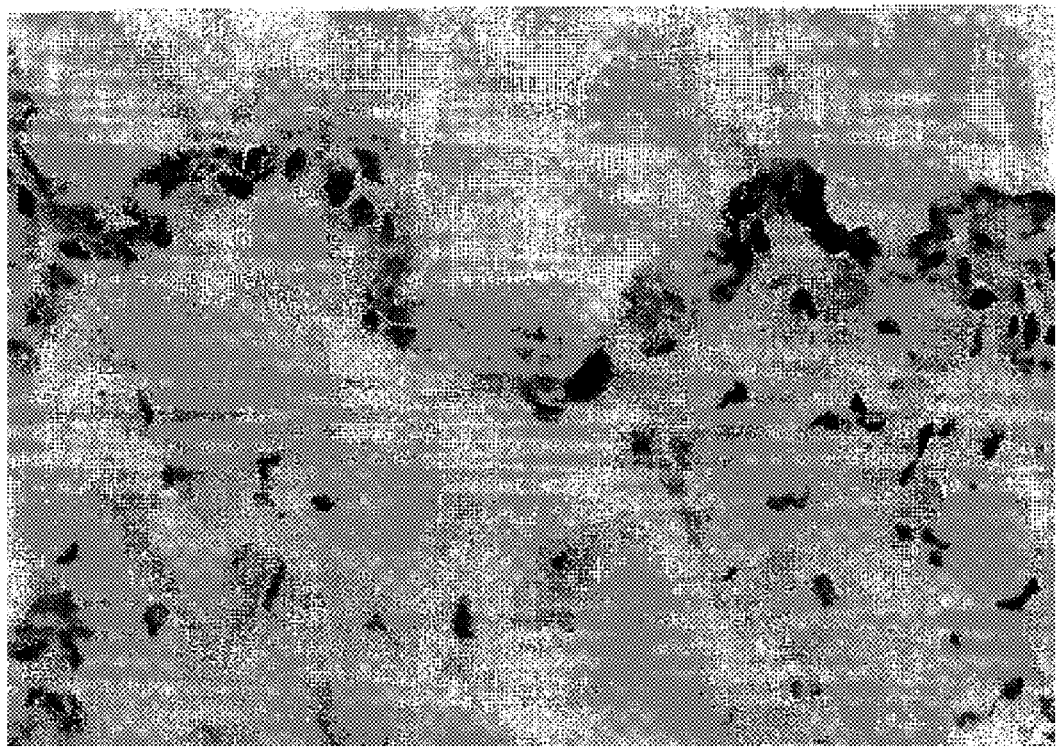

The principal target cells for non-invasive vaccination onto the skin appeared to be hair matrix cells within hair follicles (FIG. 2a) and keratinocytes within the outermost layer of epidermis (FIG. 2b) as shown by staining frozen sections with X-gal substrates after skin-targeted non-invasive delivery of an adenovirus vector encoding the E. coli β-galactosidase gene (AdCMV-βgal) (Tang et al., 1994). No physical abrasions were found in the skin tissue subjected to the treatment, and there was no inflammation induced. The skin tissue subjected to non-invasive gene delivery was excised from animals 1 day after pipetting $10^8$ pfu of AdCMV-βgal onto the skin, cross sectioned, fixed, and stained with X-gal substrates as described (Tang et al., 1994). FIG. 2a shows the adenovirus-transduced hair matrix cells within a hair follicle, x150. FIG. 2b shows the adenovirus-transduced keratinocytes within the outermost layer of epidermis, x150. No blue cells were found in control animals that were either mock-applied or coated with AdCMV-luc.

EXAMPLE 3

Elicitation of Humoral Immune Responses by Adenovirus-mediated NIVS

Figure 3A:
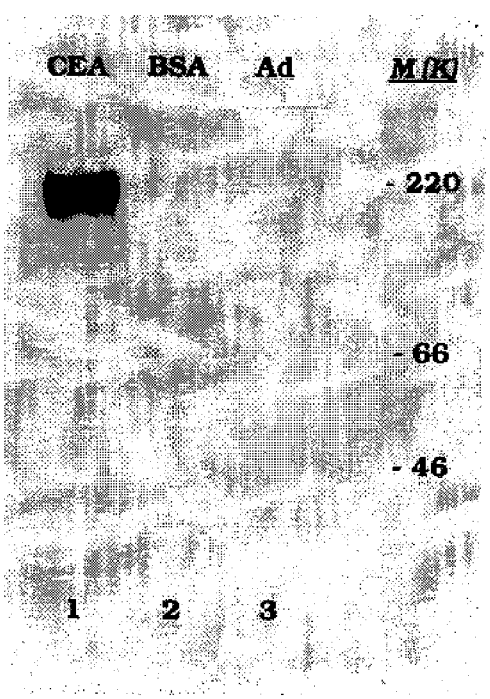
FIGS. 3a and 3b show the detection of specific antibodies in the sera of mice immunized by adenovirus-mediated NIVS.

NIVS is a novel method for vaccinating animals. To demonstrate that the procedure can elicit a specific immune response against the antigen encoded by the vector, AdCMV-hcea [an adenovirus vector encoding the human carcinoembryonic antigen (CEA)] was pipetted onto the skin of the C57BL/6 strain mice. Serum from a vaccinated mouse a month after skin-targeted non-invasive delivery of $10^8$ pfu AdCMV-hcea was diluted 1:500 and reacted with purified human CEA protein (provided by T. Strong) and adenoviral proteins that had been separated in a 5% SDS-polyacrylamide gel, and transferred to Immnobilon-P membranes (Millipore). Referring to FIG. 3a, lane 1, 0.5 μg of human CEA; lane 2, 0.5 μg of BSA; lane 3, $10^7$ pfu of adenovirus. FIG. 3a shows that the test sera from a vaccinated animal reacted in western blots with purified human CEA protein, but not with bovine serum albumin (BSA), which supports the conclusion that specific antibodies have been produced against exogenous proteins encoded by adenovirus vectors as a result of skin-targeted non-invasive gene delivery.

Figure 3B:
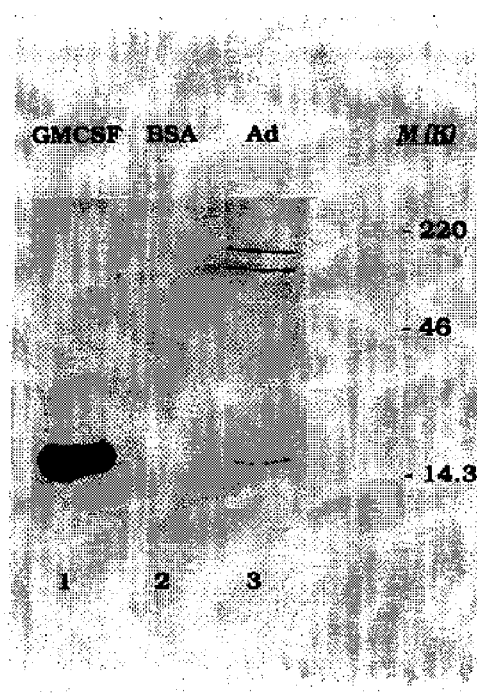

To test whether this technique might be generally applicable, AdCMV-hgmcsf [an adenovirus vector encoding the human granulocyte macrophage colony stimulating factor (hGM-CSF)] was applied onto the skin. To detect antibodies against the human GM-CSF protein, the animal was vaccinated by skin-targeted non-invasive delivery of $10^8$ pfu of AdCMV-hgmcsf. Purified human GM-CSF protein (CalBiochem) separated in a 15% SDS-polyacrylamide gel was transferred to membranes and allowed to react with diluted serum. Other treatments were carried out as described in FIG. 3a. Referring to FIG. 3b, lane 1, 0.25 μg of human GM-CSF; lane 2, 0.25 μg of BSA; lane 3, $10^7$ pfu of adenovirus. The replication-defective human adenovirus serotype 5 derived AdCMV-hcea and AdCMV-hgmcsf were produced in human 293 cells. A cassette containing the human CEA gene or the human GM-CSF gene, driven by the cytomegalovirus (CMV) early enhancer-promoter element was inserted in place of the E1a deletion. Since the sequences in the E1a region were deleted, the ability of these viruses to replicate autonomously in nonpermissive cells was impaired.

Results (Tang et al., 1997) show that 96% (23/24) of the C57BL/6 strain mice produced antibodies against the human CEA protein a month after skin-targeted non-invasive delivery of AdCMV-hcea, and 43% (6/14) of the same strain mice produced antibodies against the human GM-CSF protein after skin-targeted non-invasive delivery of AdCMV-hgmcsf. Both pre-immune sera collected before NIVS and sera from naive animals failed to react with the human CEA and GM-CSF proteins. The possibility of oral vaccination by ingesting vectors through grooming was eliminated by (1) rinsing vectors away from the skin before animals recovered from anesthesia, (2) pipetting vectors onto unshaved skin, and (3) mixing naive and vaccinated animals in the same cage. No cross-vaccination between naive and vaccinated mice was ever observed, and shaving appeared as an essential component for NIVS presumably due to the mechanical removal of cornified epithelium along the shaving path. Thus, adenovirus-mediated NIVS is capable of eliciting a humoral immune response against an antigen encoded by the vector.

EXAMPLE 4

Figure 4:
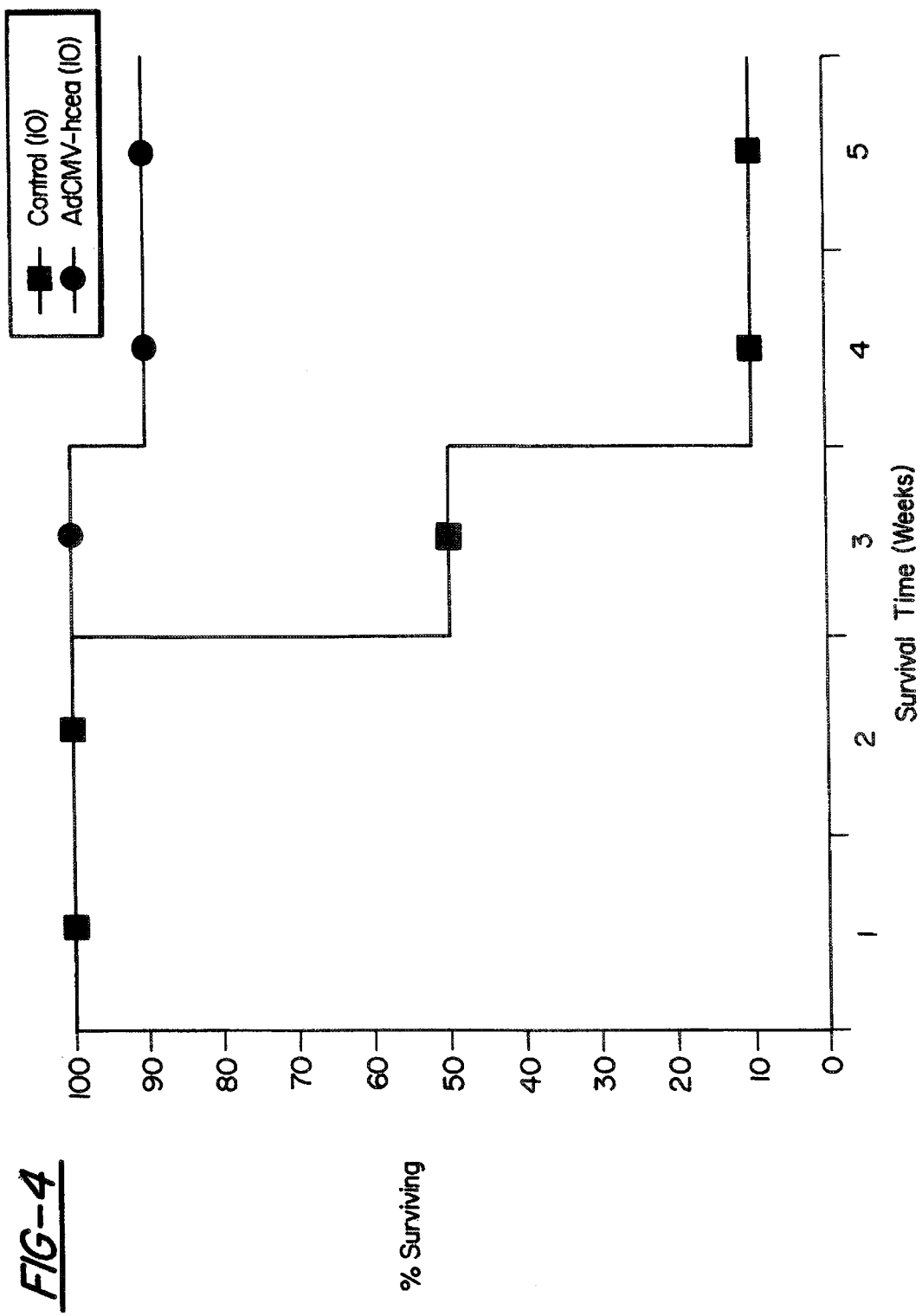
FIG. 4 shows the percent survival of control versus immunized mice that were challenged by a lethal dose of tumor cells.

To demonstrate that the techniques of the present invention can elicit a protective antitumor immune response, syngeneic tumor cells that express the human carcinoembryonic antigen (CEA) gene (MC38-CEA-2) (Conry et al., 1995) were inoculated into naive C57BL/6 strain mice and the same strain mice that had been vaccinated by topical application of an adenovirus vector encoding the human CEA gene (AdCMV-hcea). Animals subjected to tumor challenges were observed for survival (FIG. 4). In the control group, 90% (9/10) of the animals developed palpable tumor nodules and died within 30 days after tumor cell implantation. In the vaccinated group, only 10% (1/10) of the animals died, and 70% (7/10) of them remained totally tumor-free. Mice were euthanized when the tumor exceeded 1 cm in diameter. The interval between tumor cell injection and euthanization is used as the individual survival time. Referring to FIG. 4, control mice (no vaccines were administered) and animals immunized by NIVS ($10^8$ pfu of AdCMV-hcea were topically applied a month before) were subjected to tumor challenges. Numbers in parentheses represent the number of animals for each treatment. Results show that non-invasive delivery of genetic vaccines onto the skin may be able to elicit protective immune responses against tumor cells expressing a specific antigen.

EXAMPLE 5

Construction of Recombinant Adenovirus Vectors Encoding Cytokine and Co-stimulatory Genes Adenovirus vectors encoding co-stimulatory and cytokine genes were constructed for the co-delivery of these immune-modulatory genes with antigen genes into skin cells in an attempt to direct the immune profile in vaccinated animals. The adenovirus vector AdCMV-mB7.1 encoding the murine B7-1 gene and the adenovirus vector AdCMV-mgmcsf encoding the murine GM-CSF gene were constructed by homologous recombination between two transfected plasmids in human 293 cells following a standard procedure for generating new adenovirus vectors (Gomez-Foix et al., 1992). All transgenes in these vectors were transcriptionally driven by the CMV early enhancer-promoter element. AdCMV-mB7.1 was characterized by staining transduced human lung carcinoma SCC-5 cells with the anti-CD80 antibody (PharMingen), followed by flow cytometric analysis. AdCMV-mgmcsf was characterized by measuring murine GM-CSF secreted from transduced SCC-5 cells with an ELISA kit (Amersharn).

EXAMPLE 6

Detection of Antitumor Immunity by in vivo Cytotoxicity Assay

An in vivo cytotoxicity assay was developed in which target cells were implanted as monolayers onto the muscle tissue of mice (Tang et al., 1996). Implantation of target cells as monolayers allowed for an efficient retrieval of target cells for assessing their fates after a few days of in vivo growth. This assay was particularly useful for detecting weak immune responses that are not potent enough for eradicating target cells. Immune responses can be characterized by histological analysis of the implantation bed. Without an immune response, target cells would grow. With a potent immune response, target cells would be eradicated in the presence of a large number of immune effector cells at the implantation bed, probably by virtue of migration to and in situ sensitization around growing target cells. With a weak immune response, growing target cells would intermingle with infiltrating immune effector cells at the implantation bed. Implanting $5 \times 10^5$ RM1-luc cells [RM1 prostate tumor cells expressing the luciferase gene] as a monolayer into naive C57BL/6 mice resulted in a tumor layer due to proliferation of RM1-luc cells in vivo, with no evidence of immune intervention. In contrast to control animals, RM1-luc cells were intermingled with a large number of immune effector cells at the implantation bed in animals vaccinated by skin-targeted non-invasive delivery of AdCMV-luc.

EXAMPLE 7

Characterization of Immune Effector Cells Recruited by Tumor Cells

The in vivo cytotoxicity assay was able to concentrate a large number of immune effector cells at the implantation bed by implanting a small number of target cells as a monolayer onto muscle. Characterization of specific immune effector cells at the implantation bed may provide evidence as to whether a cell-mediated immune response has been elicited for killing target cells. For characterizing T cells that were recruited by luciferase-expressing tumor cells in animals vaccinated by skin-targeted non-invasive delivery of AdCMV-luc, tissue sections of the implantation bed were stained with an anti-CD3 monoclonal antibody (mAb). RM1-luc cells were produced by lipofecting pHBA-luc DNA into RM 1 prostate tumor cells (provided by T. Thompson at the Baylor College of Medicine), followed by selection in medium containing G418. Clones expressing luciferase were characterized by luciferase assay. Five×$10^5$ RM1-luc cells were implanted as a monolayer into a mouse that had been vaccinated by skin-targeted non-invasive delivery of $10^8$ pfu AdCMV-luc. Five days after implantation, the implantation bed was frozen in O.C.T. and sections were cut at 4 µm, dried in 100% acetone, and stained with an anti-CD3 mAb (clone F500A2, provided by P. Bucy at UAB), via the ABC immunoperoxidase procedure with diaminobenzidine as the chromogen.

Figure 5:
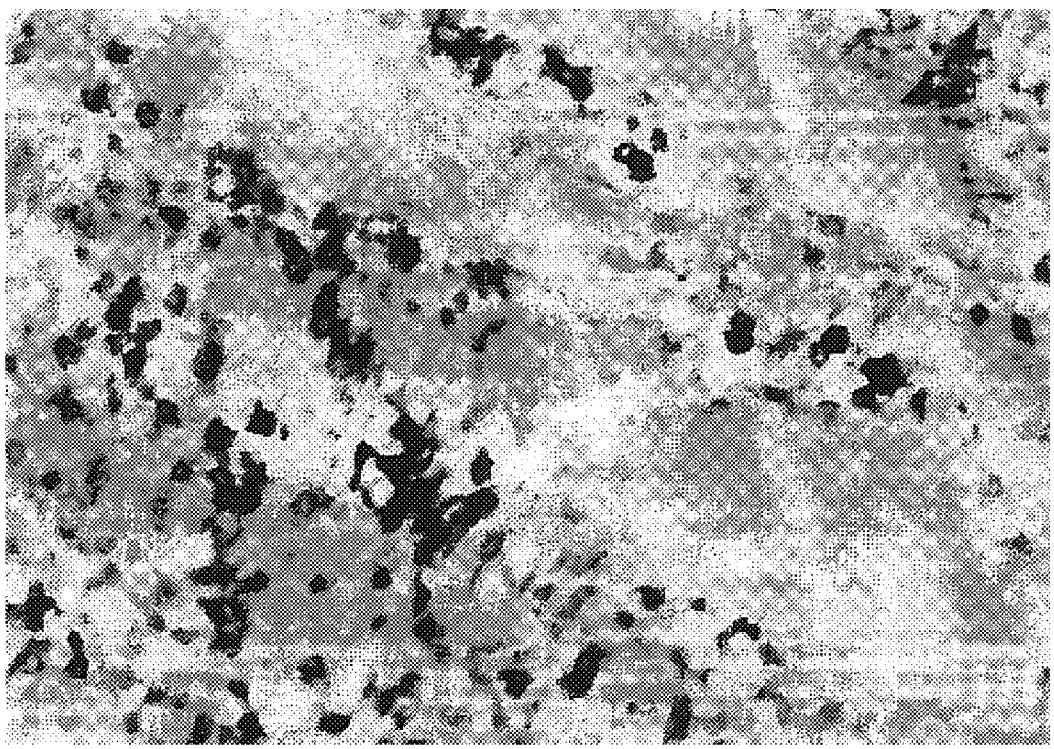
FIG. 5 shows the characterization of tumor-infiltrating T lymphocytes.

As shown in FIG. 5, a large number of T cells infiltrated into the implantation bed after 5 days of in vivo growth of RM1-luc cells in a mouse vaccinated by skin-targeted non-invasive delivery of AdCMV-luc (x150) while only a few T cells were found in naive animals. It appeared that the same number of RM1-luc target cells could recruit more T lymphocytes to the implantation bed in vaccinated animals than in naive animals.

For characterizing CTLs that were recruited by target cells, frozen sections of the implantation bed were subjected to in situ hybridization using an antisense granzyme A RNA molecule as the probe. Five×$10^5$ RM1-luc cells were implanted as a monolayer into either a naive C57BL/6 mouse or a mouse that had been vaccinated by skin-targeted non-invasive delivery of $10^8$ pfu AdCMV-luc. Five days after implantation, the implantation bed was frozen in O.C.T. and sections were cut at 4 μm. Frozen sections were fixed in 3% paraformaldehyde, incubated in 0.2 M HCl for inhibiting endogenous alkaline phosphatase activity, and hybridized with a heat-denatured antisense granzyme A RNA probe. Probes for in situ hybridization were single-stranded RNA molecules produced by transcription from a plasmid containing bacteriophage promoters. During the transcription, digoxigenin-UTP was directly incorporated into the sequence. Sense sequence probes were used as negative controls. After hybridizing with probes, sections were washed and incubated with alkaline phosphatase-conjugated anti-digoxigenin antibody, followed by incubation in the NBT/BCIP enzyme substrate solution.

Figure 6:
FIG. 6 shows the characterization of tumor-infiltrating CTLs.

CTLs that express granzyme A are activated CTLs and have been used as predictive markers for tissue rejection during transplantation. Granzyme-positive CTLs were found within the RM 1-luc implantation bed only in animals that had been vaccinated by skin-targeted non-invasive delivery of AdCMV-luc (FIG. 6). Their presence at the bed suggests that a cell-mediated immune response against tumor cells expressing a specific antigen may have been induced by NIVS.

EXAMPLE 8

Topical Application of Genetic Vaccines by Adhesive Bandages

It was demonstrated, for the first time, that bandages could be used for the administration of vaccines. This development may allow personnel without medical training to deliver a uniform dose of non-invasive vaccines onto the skin. To transduce skin by bandage, 50 μl of the AdCMV-luc vector described in Example 7 was pipetted into the pad of an adhesive bandage (Johnson & Johnson). The vector-containing bandage was subsequently adhered to pre-shaved skin of a mouse. The vector was kept in contact with naked skin for 18 hours. To detect transgene expression from genetic vectors delivered by a bandage, the skin was assayed for luciferase (Table 1). While the results show substantial variation, transgene expression in the skin was achievable using adhesive bandages.

Figure 7:
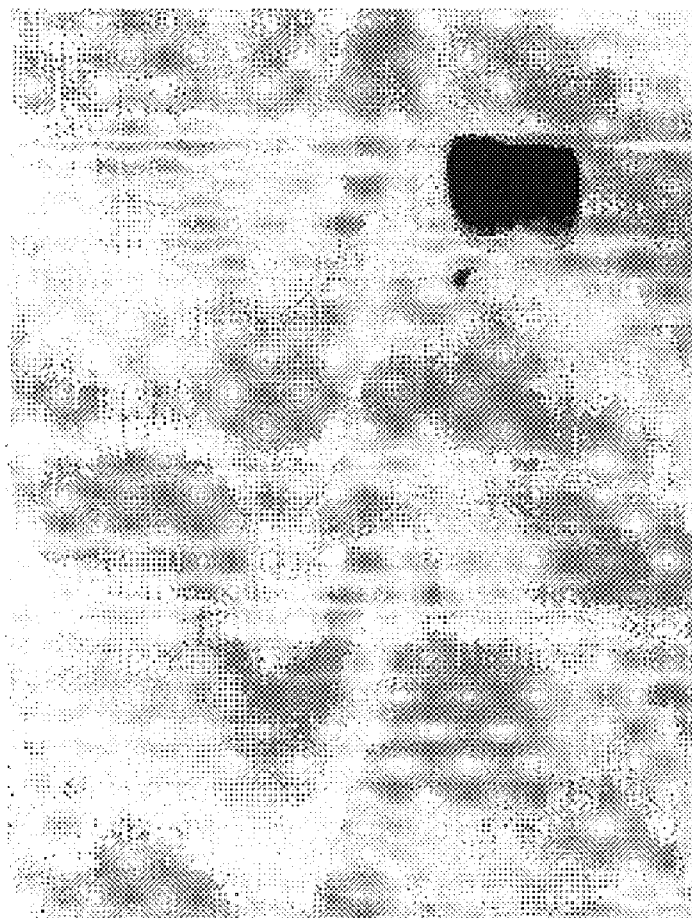
FIG. 7 shows the western blot analysis of antibodies to the human CEA protein in mice immunized by topical application of vaccine bandages.

To demonstrate that animals could be vaccinated with non-invasive adhesive bandages, sera from tail bleeds were assayed for anti-CEA antibodies two months after adhering bandages containing AdCMV-hcea onto the skin of mice. As shown in FIG. 7, anti-CEA antibodies were detected in 100% (10/10) of mice that received non-invasive vaccines through adhesive bandages.

EXAMPLE 9

DNA/Adenovirus-mediated NIVS

Adenovirus-based vectors can be made more versatile by binding plasmid DNA to the exterior of an adenovirus. The resulting vector system mediates high-efficiency gene delivery to a wide variety of target cells. This approach allows greatly enhanced flexibility in terms of the size and design of foreign genes. DNA/adenovirus complexes may thus be able to deliver antigen genes into the skin via the same adenovirus receptor-mediated endocytosis pathway with more flexibility.

Figure 8A:
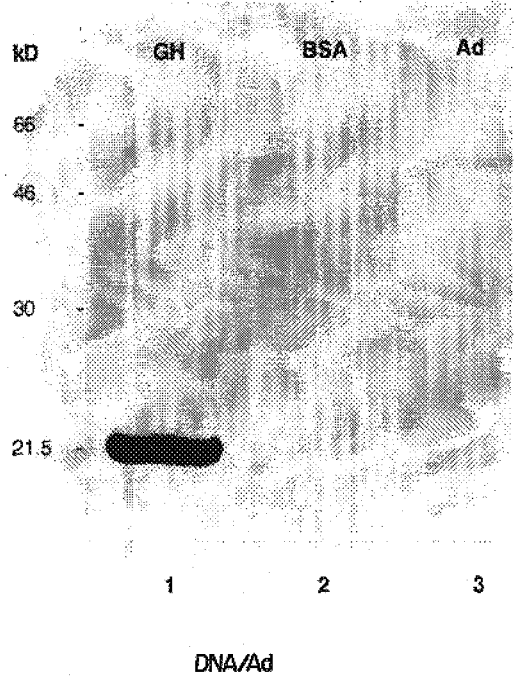
FIG. 8a shows the detection of specific antibodies in the serun of a mouse immunized by DNA/adenovirus-mediated NIVS.

To demonstrate the feasibility of DNA/adenovirus-mediated NIVS, plasmid DNA encoding the human growth hormone (pCMV-GH) (Tang et al., 1992) was allowed to complex with an E4-defective adenovirus. Mice (strain C57BL/6) were vaccinated by contacting DNA/adenovirus complexes with naked skin for one day. Immunized animals were subsequently monitored for the production of antibodies against the human growth hormone protein (hGH) by assaying sera from tail-bleeds. As shown in FIG. 8a, lane 1, hGH (0.5 μg); lane 2, BSA (0.5 μg), the test sera reacted in western blots with purified hGH, but not with irrelevant proteins. Of ten mice vaccinated by DNA/adenovirus complexes, eight (80%) produced antibodies against hGH within three months, indicating that specific antibodies could be produced against exogenous proteins encoded by plasmid DNA that is complexed with adenovirus and administered in a non-invasive mode. Pre-immune sera collected before treatment, sera from untreated animals, and sera from animals vaccinated with irrelevant vectors all failed to react with hGH. Thus, DNA/adenovirus complexes, like adenovirus recombinants, appear as a legitimate vector system for NIVS.

EXAMPLE 10

DNA/Liposome-mediated NIVS

Figure 8B:
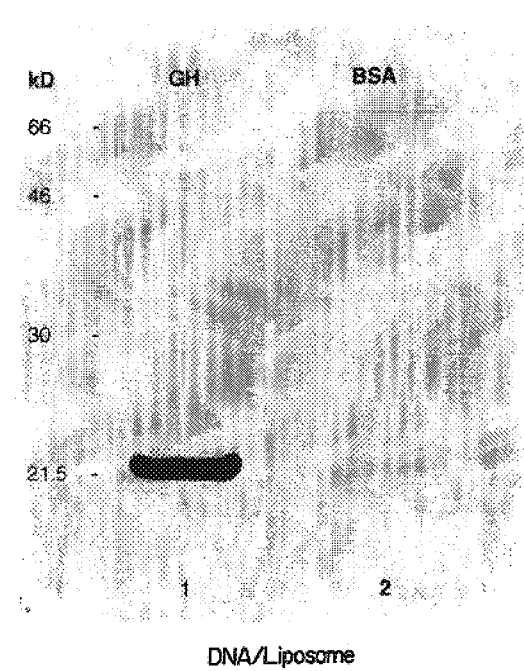
FIG. 8b shows the detection of specific antibodies in the serum of a mouse immunized by DNA/liposome-mediated NIVS.

In addition to developing genetic vectors involving adenovirus as carriers for non-invasive vaccines, it has also been demonstrated that mice could be vaccinated by topical application of DNA/liposome complexes without viral elements. It is apparent that many different vectors can be applied in a creative way for the administration of skin-targeted non-invasive vaccines. As shown in FIG. 8b, lane 1, hGH (0.5 μg); lane 2, BSA (0.5 μg), the test serum from a mouse immunized by topical application of DNA/liposome complexes encoding hGH reacted with hGH but not with BSA. Of 10 mice vaccinated by DNA/liposome complexes, the test sera reacted with purified hGH in 9 (90%) treated animals within 5 months. Thus, the DNA/liposome complex, like the adenovirus and the DNA/adenovirus complex, appears as another legitimate vector system for NIVS.

EXAMPLE 11

Co-expression of DNA-encoded and Adenovirus-encoded Transgene

Strategies of augmenting the immune system's response can potentially improve the clinical outcomes of vaccines. Local production of immune-modulatory molecules involved in the activation and expansion of lymphocyte populations may significantly improve the vaccination effects. Adenovirus vectors encoding the murine B7-1 and GM-CSF genes have been made. Topical application of DNA/adenovirus complexes may thus be able to co-express DNA-encoded antigens or immune modulatory molecules with adenovirus-encoded antigens or immune modulatory molecules in individual skin cells for enhancing the immune response against the antigen.

Figure 9:
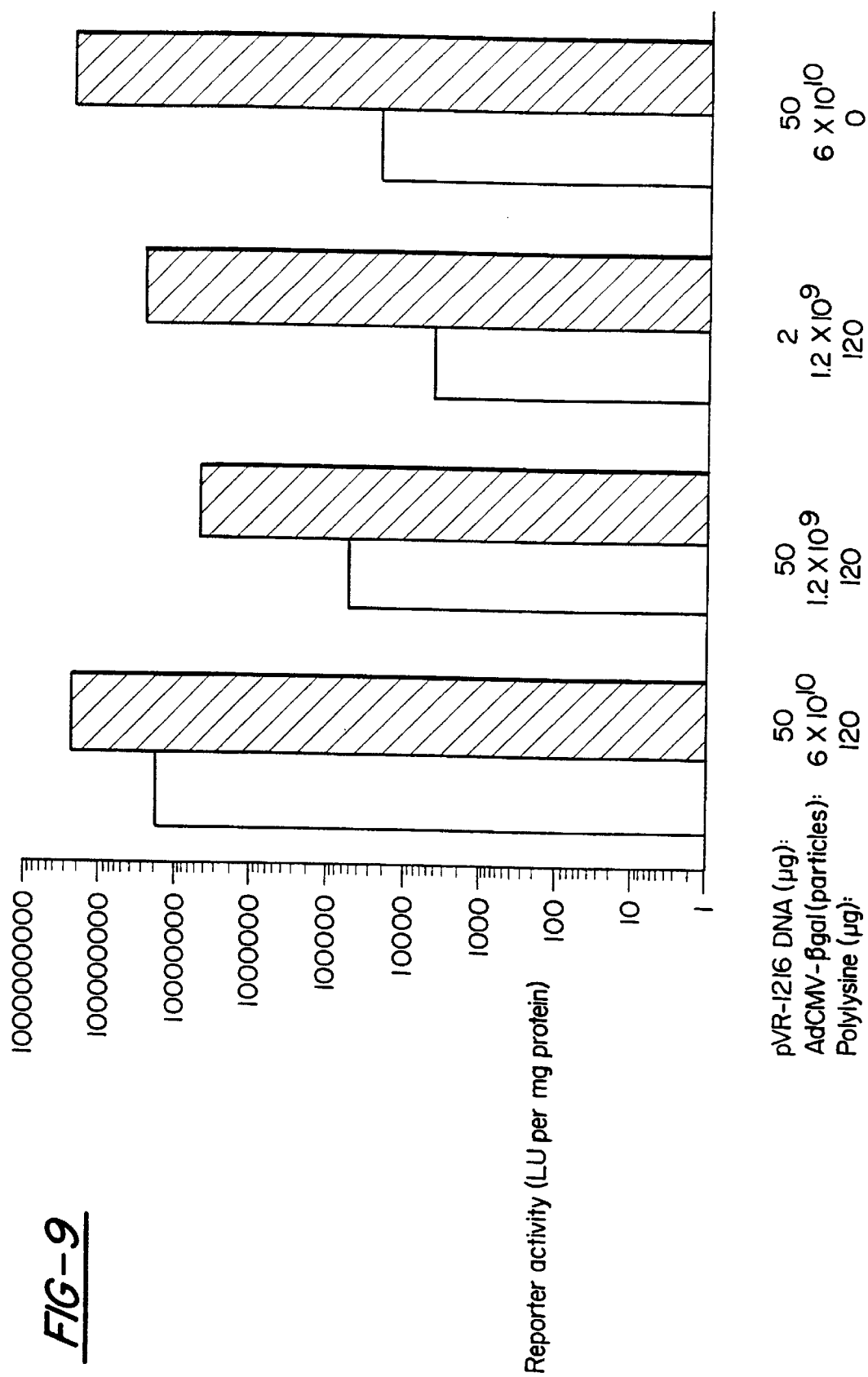
FIG. 9 shows the co-expression of DNA-encoded and adenovirus-encoded transgenes in target cells.

FIG. 9 shows that the expression of transgenes from plasmid DNA in target cells is dependent upon the presence of adenovirus, thus allowing plasmid-encoded and adenovirus-encoded transgenes to be co-expressed in the same cell. pVR- 1216 plasmid DNA (provided by Vical), AdCMV-$\mu$gal particles and polylysine were mixed at specific ratios as shown in the figure. The complex was applied to $2 \times 10^5$ SCC-5 cells in a well and incubated for 2 hours. The complex was then removed and cells were harvested for luciferase and $\mu$-galactosidase assays the next day. Open column: luciferase activity; solid column: $\mu$-galactosidase activity. Results show that DNA-encoded transgenes are not expressed in target cells in the absence of adenovirus, whereas adenovirus-encoded transgenes can be expressed in the presence of DNA. It is also possible that DNA may be condensed onto the surface of other viruses for targeting different cell types. Accordingly, this protocol provides a simple but versatile gene delivery system which allows the expression of transgenes from both a virus recombinant and an externally-bound plasmid, simultaneously.

Figure 10:
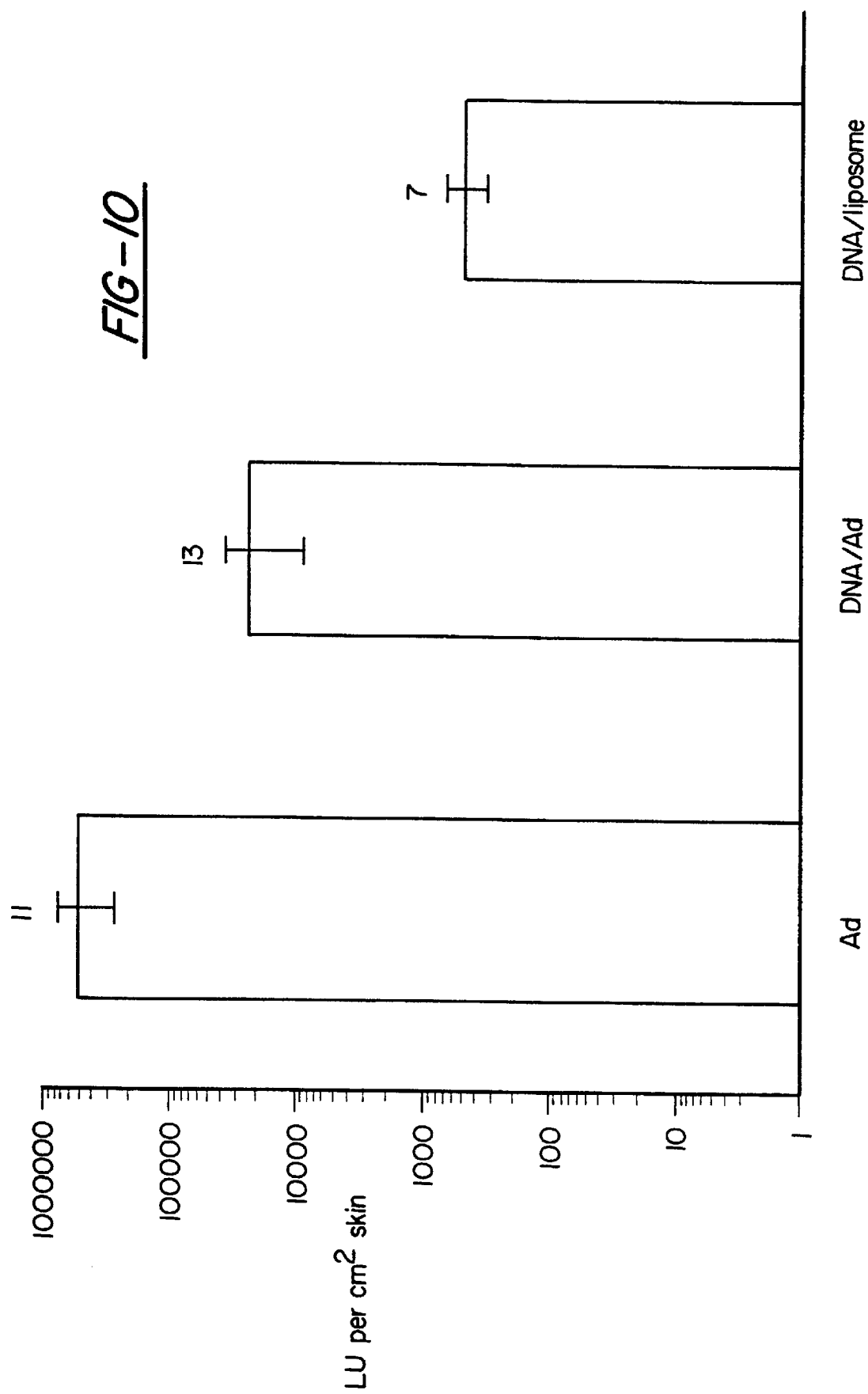
FIG. 10 shows relative transgene expression from topically-applied adenovirus recombinants, DNA/adenovirus complexes, and DNA/liposome complexes.

Relative Transgene Expression in the Skin from Different Genetic Vectors by Topical Application It has been shown that adenovirus recombinants, DNA/adenovirus complexes, DNA/liposome complexes, and perhaps many other genetic vectors can all be applied as carriers for non-invasive vaccines. It is conceivable that the higher the efficiency for transgene expression, the more powerful the carrier will be. To define the relative efficiencies for the vectors utilized, adenovirus recombinants, DNA/adenovirus complexes, or DNA/liposome complexes were allowed to contact mouse skin by topical application for 18 hr. The treated skin was subsequently removed from the animal and assayed for luciferase activity with a luminometer by measurement of integrated light emission for 2 min using the Promega's luciferase assay system, and background was subtracted from the readings. As shown in FIG. 10, adenovirus recombinants were found to be the most efficient vector system for skin-targeted non-invasive gene delivery. Mice mock-treated produced no detectable luciferase activity in the skin. LU, light units; Ad, AdCMV-luc; DNA/Ad, pVR-1216 DNA complexed with Ad dl1014; DNA/liposome, pVR-1216 DNA complexed with DOTAP/DOPE. Results are the mean log[LU per cm$^2$ skin]±SE (n is shown on top of each column). Although the efficiency of DNA/adenovirus complex is lower than that of adenovirus recombinant, it is significantly higher than that of DNA/liposome complex. In addition, adenovirus may be inactivated by UV irradiation before complexing with DNA to prevent viable viral particles from disseminating. Thus, DNA/adenovirus complexes may appear as the most promising carrier system for the delivery of non-invasive vaccines when efficiency and safety factors are both considered in formulating a new generation of vaccines.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

REFERENCES

The following references were cited herein:
Barry, M. A. et al. Protection against mycoplasma infection using expression-library immunization. *Nature* 377, 632–635 (1995).
Conry, R. M. et al. A carcinoembryonic antigen polynucleotide vaccine for human clinical use. *Cancer Gene Ther.* 2, 33–38 (1995).
Cotten, M. et al. High-efficiency receptor-mediated delivery of small and large (48 kilobase) gene constructs using the endosome-disruption activity of defective or chemically inactivated adenovirus particles. *Proc. Natl. Acad. Sci USA* 89, 6094–6098 (1992).
Glenn, G. M. et al. Skin immunization made possible by cholera toxin. *Nature* 391, 851 (1998).
Gomez-Foix et al. Adenovirus-mediated transfer of the muscle glycogen phosphorylase gene into hepatocytes confers altered regulation of glycogen metabolism. *J. Biol. Chem.*, 267, 25129–25134 (1992).
Johnston, S. A. & Tang, D.-c. Gene gun transfection of animal cells and genetic immunization. *Meth. Cell Biol.* 43, 353–365 (1994).
McDonnell, W. M. & Askari, F. K. DNA vaccines. *New Engl. J. Med.* 334, 42–45 (1996).
Tang, D.-c. et al. Genetic immunization is a simple method for eliciting an immune response. *Nature* 356, 152–154 (1992).
Tang, D.-c. et al. Butyrate-inducible and tumor-restricted gene expression by adenovirus vectors. *Cancer Gene Ther.* 1, 15–20 (1994).
Tang, D.-c. et al. In vivo cytotoxicity assay for assessing immunity. *J. Immunol. Methods* 189, 173–182 (1996).
Tang, D.-c. et al. Vaccination onto bare skin. *Nature* 388, 729–730 (1997).

TABLE 1

| Incubation time (hours) | LU per cm$^2$ skin |
|---|---|
| 1 | 0 |
| 1 | 2,100 |
| 2 | 0 |
| 2 | 0 |
| 2 | 6,200 |
| 2 | 7,300 |
| 2 | 13,000 |
| 2 | 48,000 |
| 2 | 1,800 |
| 2 | 13,000 |
| 18 | 830 |
| 18 | 2,400 |
| 18 | 260 |
| 18 | 630 |
| 18 | 1,300,000 |
| 18 | 24,000 |
| 18 | 2,700 |
| 18 | 280 |

What is claimed is:

1. A method of non-invasively inducing a systemic immune response, comprising topically administering, a plasmid DNA and liposome complex vector that encodes a gene of interest and expresses a protein encoded by the gene of interest, to the skin of a mammal, in an effective amount to induce said systemic immune response to said protein, wherein a systemic immune resonse to said protein is induced in said mammal.

2. The method of claim 1, wherein said mammal is shaved at the site of the topical administration.

3. A method of non-invasively inducing a protective systemic immune response, comprising topically administering, a DNA vector that encodes a gene of interest and expresses a protein encoded by the gene of interest, to the skin of a mammal, in an effective amount to induce said protective systemic immune response to said protein, wherein a systemic immune response to said protein is induced in said mammal; and, wherein said protein comprises an antigen or immunogenic fragment thereof.

* * * * *